United States Patent [19]
LeClerc

[11] Patent Number: 5,605,993
[45] Date of Patent: Feb. 25, 1997

[54] DERIVATIVES OF POLYETHERS AND OF PENTACYCLIC HETEROCYCLES, THEIR POLYMERS AND THEIR APPLICATIONS, PARTICULARLY TO THE COMPLEXING OF METAL IONS

[75] Inventor: Olivier LeClerc, Moret Sur Loing, France

[73] Assignee: Electricite De France-Service National, Paris, France

[21] Appl. No.: 473,112

[22] Filed: Jun. 7, 1995

Related U.S. Application Data

[62] Division of Ser. No. 274,784, Jul. 14, 1994.

[30] Foreign Application Priority Data

Jul. 16, 1993 [FR] France ................................ 93 08789

[51] Int. Cl.$^6$ .................. C08F 128/06; C08F 126/06; C08F 116/12; C25D 9/02; B01D 39/00
[52] U.S. Cl. ................... 526/256; 526/258; 526/333; 205/317; 210/500.28
[58] Field of Search ................... 526/256, 258; 205/317; 210/500.28

[56] References Cited

U.S. PATENT DOCUMENTS 5,200,041  4/1993  Simonet et al. ................. 204/78

Primary Examiner—Joseph L. Schofer
Assistant Examiner—Wu C. Cheng
Attorney, Agent, or Firm—Antonelli, Terry, Stout & Kraus

[57] ABSTRACT

It concerns a monomer, a polymer obtained from the monomer and a process for obtaining the said polymer. The monomer consists of a polyether containing at least 3 ether units and pyrrole or thiophene units bonded to the ends of the chains of this polyether via, for each of these heterocycic compounds, either their carbon atoms in the 3,3'-positions of their heterocycles or, as regards more particularly the pyrrole groups, via their respective nitrogen atoms, the 2- and 2'-positions of these heterocycles being, however, free of all substitutions or, at the very most, substituted by easily removable groups (protective groups, for example).

Application to the purification and recovery of metal ions such as radioactive silver.

4 Claims, 4 Drawing Sheets

DERIVATIVES OF POLYETHERS AND OF PENTACYCLIC HETEROCYCLES, THEIR POLYMERS AND THEIR APPLICATIONS, PARTICULARLY TO THE COMPLEXING OF METAL IONS

CROSS-REFERENCE TO RELATED APPLICATIONS

This application is a Divisional application of application Ser. No. 274,784, filed Jul. 14, 1994.

BACKGROUND OF THE INVENTION

Salts of polymers of compounds of aromatic nature possessing complexing cavities have already been produced by molecular electrochemistry techniques (1), these techniques involving an electrodeposition of certain polytriphenylenes on essentially non-corrodible supports, such as precious metals (platinum, gold) or vitreous carbons. The most common example relates to the polymerization of the compound known under the name DB-18-C-6 (I) to polytriphenylene:

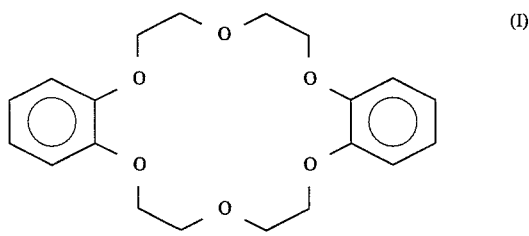

(I)

The direct formation of a doped form of the polymer (doubtless of redox nature) has been demonstrated. These polymer salts can be easily reduced or "dedoped" by chemical agents such as tertiary amines or tetraalkylammonium hydroxides. It is possible, in this way, to obtain neutral, non-conductive resins which are resistant to chemical agents and to solvents, which have an electronic conductivity and which have both polyaromatic linkages and polyether units, obtained from certain biaromatic polyethers (II),

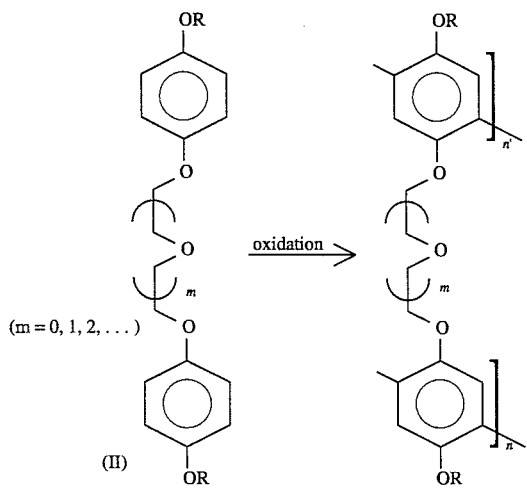

in which the anodic activation is increased by the presence of donor groups on the aromatic systems (example: ether groups). When the polymerization is carried out at a sufficiently oxidizing potential, conductive polyparaphenylenes can be obtained by virtue of the high concentration of redox sites produced in the matrix (oxidation at 4 electrons per monomer unit). These redox sites make the material sufficiently permeable to the flows of electrons necessary for the growth in thickness of the films formed, by virtue of the electron jumps induced between these sites, during the development of the deposits. It has already been proposed to use such polymers for extracting certain metal ions present in aqueous or organic solutions brought into contact with them (2). However, they are not always effective, as regards, for example, removing (or recovering) traces of silver contained in certain effluents. The production costs are high. Difficulties also accompany the synthesis of the monomers, especially from hydroquinones, and then the oxidation of these monomers, which must be carried out at a fairly strongly oxidizing potential even if the aryl groups have been activated beforehand.

SUMMARY OF THE INVENTION

The aim of the invention is the production of new monomers which are more easily accessible than the aromatic polyethers of the type mentioned above and which are polymerizable by the use of molecular electrochemistry techniques of the abovesaid type but at less oxidizing potentials. Consequently, another aim of the invention is the easy extension of these techniques to other categories of conductive supports more sensitive to oxidation than the precious metals indicated above. In particular, the aim of the invention is the formation, more easily than previously, of deposits of this type on graphite supports. The use of the latter as a support for aromatic polyethers of type II was difficult, due to the ability of the graphite to be at least partially converted to graphite salts at relatively low oxidation potentials, sometimes below the potentials required for obtaining an electrodeposition of the corresponding polymers.

A further aim of the invention is the production of polyether derivatives which are particularly efficient as regards their ability to remove traces of certain metals, in concentrations below $10^{-10}$M, indeed even $10^{-12}$M. In particular, the metals in question are those whose sequestration or encapsulation is being sought: particularly the transition metals, zinc, cadmium, silver and the like or radioactive metal elements.

The monomers according to the invention, which are also polymerizable by molecular electrochemistry techniques, consist of polyethers containing at least three ether units and carrying pyrrole or thiophene units bonded to the ends of the chains of these polyethers via, for each of these heterocyclic compounds, either their carbon atoms in the 3,3'- positions of their heterocycles or, as regards more particularly the pyrrole groups, via their respective nitrogen atoms, the 2- and 2'-positions of these heterocycles being, however, free of all substitutions or, at the very most, substituted by easily removable groups (protective groups, for example).

The polyether chains which form part of the constitution of the monomers according to the invention are preferably linear and contain ether units, preferably of the type $-[(CH_2)_p-O-]_n-$ with p being an integer of 2 or 3 and n being an integer from 3 to 5, these chains then being connected at the $\alpha$- and $\omega$-positions to pyrrole or thiophene units under the conditions indicated above.

In particular, these chains are of the type:

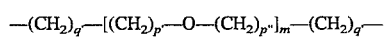

$-(CH_2)_{q'}-[(CH_2)_p-O-(CH_2)_{p''}]_m-(CH_2)_{q''}-$ with q' and q" being, independently of one another, equal to 1 or 2, p and p" being, independently of one another, equal to 1 or 2, and m is equal to 3, 4 or 5.

The invention more particularly relates to new monomers of formula:

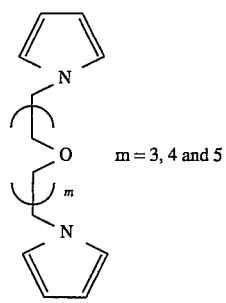

(III)

m = 3, 4 and 5

Such monomers are capable of being obtained easily by reaction of an alkali metal salt of pyrrole, particularly pyrrolylpotassium, with a dihalogenated derivative of the glycol corresponding to the final polyether chain. For example, the corresponding glycol will have been converted beforehand to the dichlorinated derivative by reaction with thionyl chloride.

Other categories of preferred monomers in accordance with the invention are characterized by one or other of the following structures:

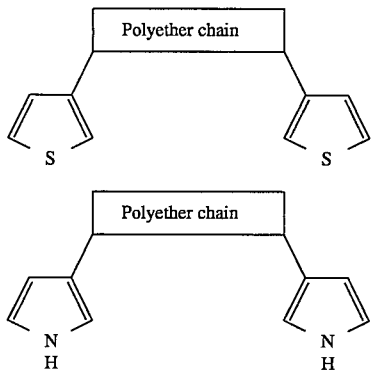

(IV)

(V)

and more particularly those corresponding to the following formula:

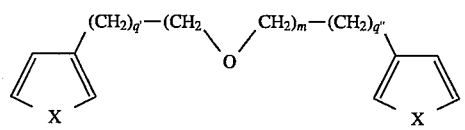

(VI)

with X being an NH group or a nitrogen or sulphur atom q' and q" being, independently of one another, equal to 1 or 2 and m being equal to an integer from 3 to 5.

The advantage of such molecules in the anodic polymerization process is to give rise to very much larger heterogeneous polymerisation yields [(weight of electrodeposited resin/monomer mass ratio)×100]. It is advisable to leave the 2,2'-positions on the pyrrole and thiophene rings free so as not to slow down the polymerization process.

Thus, with the thiophenes and when p=0 and p'=0, the coupling of a polyether chain can be carried out without problems from 3-bromothiophene in accordance with the reaction model developed below.

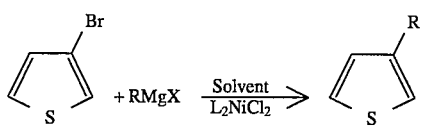

This reaction is carried out at ordinary temperature in ether or THF for 24 hours. X in the starting halide RX=Cl or Br.

L is a ligand of the phosphine type (Ref.: M. KUMADA et al., J. Org. Chem., (1981), 46, 4481 and J. P. MONTHEARD et al., Synth. Comm., (1984), 14, 289). In this case, the organo magnesium derivative formed will be a "diorganomagnesium" derivative of the type $R'(MgX)_2$ which can be easily prepared from α,ω-diols containing a polyether chain and dichlorinated with thionyl chloride.

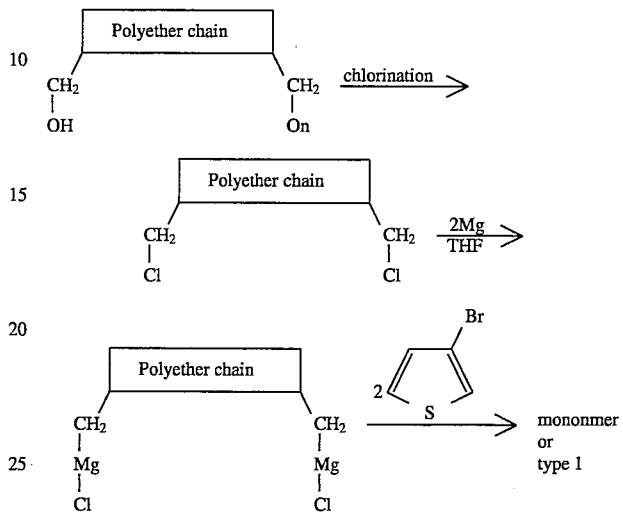

The substitution reaction in the 3-position of the pyrroles (in particular in the case where p=0 and p'=0) is, in principle, more problematic because it assumes a priori the protection of the N—H— functional group. A possible procedure is the protection by a sulphonyl chloride (R=methyl or phenyl):

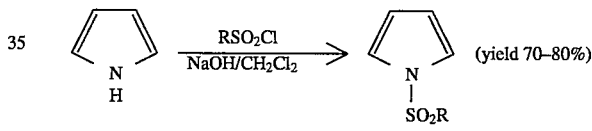

Phase transfer catalysis and then carrying out a Friedel-Crafts reaction with acetyl chloride in the presence of aluminium chloride. The ketone is then reduced to the corresponding alcohol by lithium aluminium hydrate with a good yield.

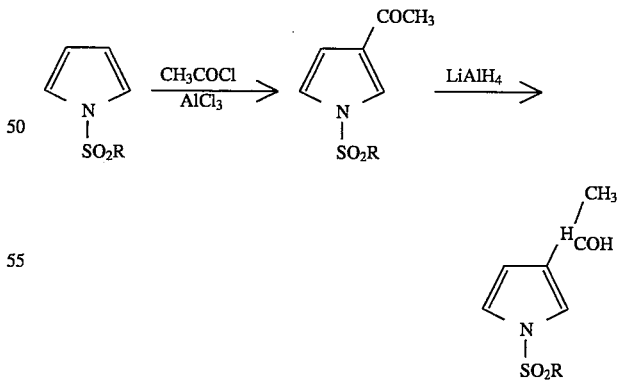

The etherification reaction is carried out in THF in the presence of sodium hydride while the ditosylate of the polyether diol is progressively added. Deprotection of the amino functional group of the pyrrole is then carried out conventionally by phase transfer catalysis (presence of a base in two-phase medium in the presence of a detergent, such as that marketed under the trade name Triton B).

The introduction of acid groups (carboxy and sulpho) in the 3'-position on the pyrrole and the thiophene makes it possible to greatly reinforce the ion-exchange resin nature of this type of polymer.

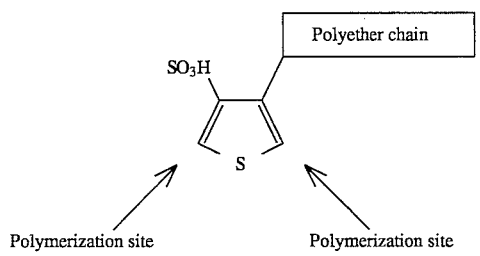

However, the difficulty relating to the synthesis of such monomers a priori excludes their use. It is preferred to carry out a copolymerization of:

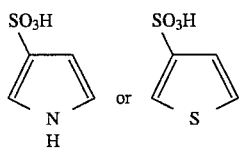

with the polyether monomers 1 or 2 in equimolecular mixtures (there is thus statistical introduction of 0.5 sulpho group per aromatic ring).

In the case of the compounds of formula VI in which p and p' are other than 0, the initial corresponding thiophene or pyrrole compounds will advantageously have OH groups in the 2- and 2'-positions respectively which are then capable of taking part in a reaction with a polyether ditosylate corresponding to the polyether chain which must bind these heterocycles together.

The invention also relates to the oligomers (including dimers) and the polymers capable of being produced from the abovesaid monomers, these polymers being characterized by polymeric chains containing a plurality of pyrrole or thiophene rings, if appropriate both at the same time, and interconnected to each other via 2,2'-bonds, on the one hand, and polyether chains, corresponding in particular to the formulae $-CH_2-(-CH_2-O-CH_2-)_m-CH_2-$ with m equal to 3, 4 or 5, these chains being themselves bonded by their own ends either to the carbon atoms in the 3,3'-positions respectively of these pyrrole or thiophene rings or, in the case of the pyrrole rings, to their nitrogen atoms.

A process for the production of these polymers comprises the electrodeposition of the polymer on an anode of an electrolysis cell, or on a conductive support material, particularly carbon-based, in electrical contact with this anode, from an electrolyte containing the monomer as defined above and from a salt capable of giving rise to a non-oxidizable anion, under a potential which allows a polymerization of the monomer on contact with the anode or, when it is present, with the support material, the abovesaid monomers and salts being in the dissolved state in a polar or dipolar organic solvent, this solvent and the support being respectively chosen from those which themselves have a sufficient resistance to oxidation under the abovesaid potential.

It goes without saying that this process must be implemented in the absence of any trace of the specific metal or metals, particularly alkali metals or alkaline-earth metals, transition metals, zinc, cadmium, silver and the like or radioactive elements, when the polymers produced are intended to be used for the sequestration or encapsulation of these metals, particularly in the form of metal ions, more particularly in the trace condition, in liquid media brought into contact with them for purposes either of purification or of recovery.

The polymerization of the dipyrrole or dithiophene monomers can be carried out on any non-corrodible surface such as platinum, gold or rhodium. Depositition is also possible on all vitreous carbons and various types of graphite [natural or "HOPG" (abbreviation of the expression "Highly oriented pyrolytic graphite")]. It can be easily carried out in the usual polar and dipolar organic solvents, if they have a reduced electrochemical activity (by significant oxidation of the solvent before +1.2 V/Ag/Ag$^+$). Thus, technical grade acetonitrile can easily be used but dichloromethane and nitromethane can also lead to the polymerization of the pyrroles. The electrolyte must essentially contain a non-oxidizable anion. Thus, tetraalkylamonium (alkyl=Me, Et, Pr, Bu, Hex, d and the like) and alkali metal (lithium, sodium or potassium) perchlorates, hexafluorophosphates, tetrafluoroborates, hexafluoracetates and the like are all electrolytes which can be used. The choice of the salt can be guided by the solubility in the solvent under consideration. The polymers are deposited particularly well. They can be obtained on the various forms of carbon, in particular graphite, and can be obtained in the form of much thicker deposits than on precious metals.

The invention also obviously relates to the polymers supported by these conductive supports, particularly based on carbon and more particularly on graphite. The use of carbon, in particular graphite, supports is of particular advantage, taking into account the ability of these materials to be brought under various forms, particularly as porous grains which can then be charged with polymers.

The invention also naturally relates to the applications which can be made of these polymers in the supported or non-supported state. In particular, the invention relates to the application of these polymers as sequestration or "encapsulation" agents for metal ions, more particularly resulting from transition metals, zinc, cadmium, silver and the like, contained in solutions brought into contact with them, for purposes either of purification of these solutions or else of recovery of the corresponding metals. The polymers of the type in question may then be regarded as "polymer-cages" with respect to these ions.

The low molecular weight oligomers, and more particularly the dimers, particularly cyclic dimers which are fairly soluble in organic solvents, can, for this reason, be the object of various industrial applications: phase transfer catalysis, application to the separation of rare-earth metals, and the like.

Other characteristics of the invention will become further apparent in the course of the description which follows of certain examples which have no other objective than that of illustrating the invention without limiting it in any way.

EXAMPLES

DETAILED DESCRIPTION OF THE INVENTION

A) Preparation of the Monomers (III)

Figure 1A:
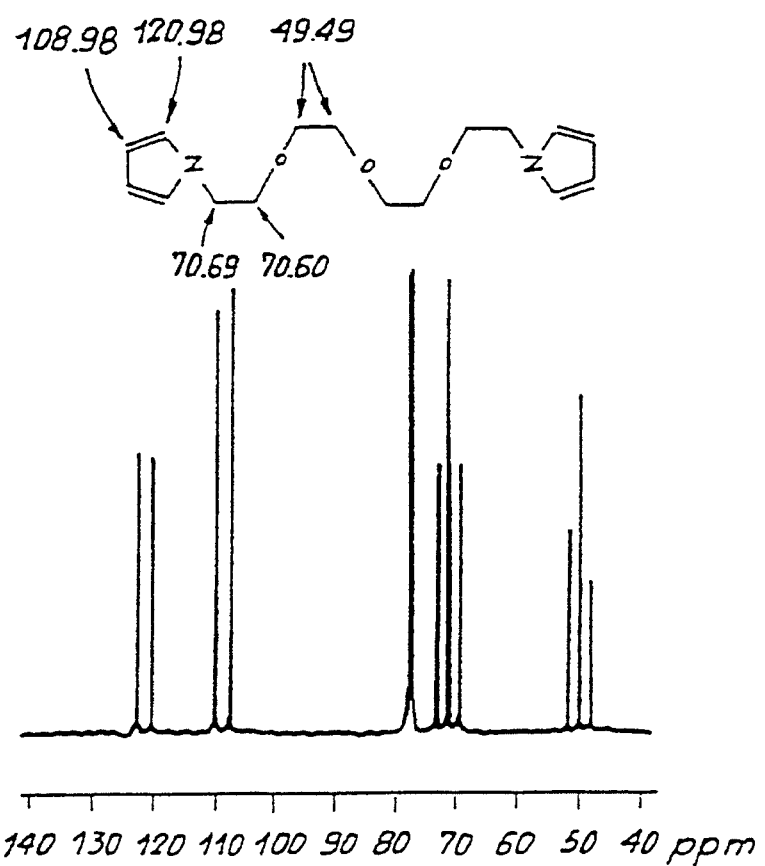
FIG. 1 shows nuclear magnetic resonance spectra relating to a specific monomer in accordance with the invention $^{13}$C NMR spectra, 75 MHz, CDCl$_3$, δ(ppm/TMS)

The method of synthesis applicable to all the polyethers ($1 \leq m \leq 5$) is described below.

1. Typical synthesis example for the triether (m=3):1-11bis(1-1 pyrrole) 3,6,9 trioxaundecane It is advisable first of all to synthesize potassium pyrrole:

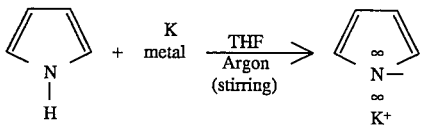

40 ml of THF, treated beforehand with the benzophenone-sodium system in order to remove peroxides, are placed in a 250 ml, 3-necked, round-bottomed flask. 8 g of potassium ($2.05 \cdot 10^{-1}$ mol) are added in small portions. 14.42 g of pyrrole ($2.15 \cdot 10^{-1}$ mol) are then added dropwise via a dropping funnel. The mixture is left stirring (at room temperature) in an inert atmosphere (argon) for 24 hours. The contents are filtered, washed with ether and then dried. 16.5 g of dry salt are obtained in this way (yield approximately 75%).

The bielectrophile is obtained at the same time by treatment of tetraethylene glycol with $SOCl_2$ according to the procedure described by C. J. Pedersen (J. Am. Chem. Soc. (1967), 89, 7017):

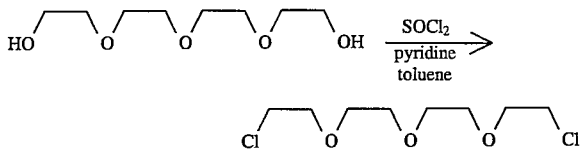

The reaction is carried out in a 500 ml round-bottomed flask (with reflux condenser, nitrogen inlet, thermometer and dropping funnel) in which 43 g of tetraethylene glycol (0.22 mol), 200 ml of toluene and 38.6 g of pyridine (0.49 mol) are placed. The mixture is brought, with stirring, to 85° C. and 58 g of thionyl chloride (0.49 mol) are added very slowly. This requires approximately 4 hours; the temperature of the reaction mixture is subsequently maintained at 80° C. for 20 hours. An HCl solution (5 ml of concentrated acid in 20 ml of water) is then added. Separation is carried out by settling, washing is carried out with water and drying is carried out over $CaCl_2$. 46 g of crude liquid are obtained in this way. 40 g of pure dichlorinated product are isolated by vacuum distillation (yield 80%). Condensation of the pyrrole salt with the bielectrophile is then carried out in order to yield the monomer.

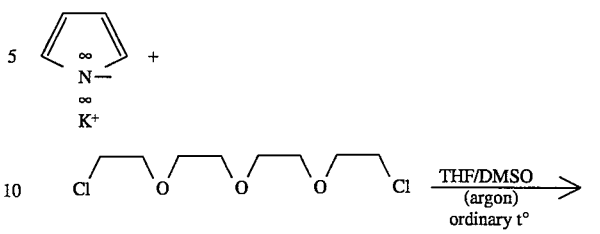

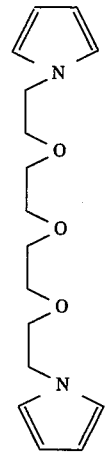

The condensation is carried out in a 250 ml, 3-necked, round-bottomed flask in which there are placed:

25 ml of dimethyl sulphoxide (DMSO)

15.75 g K pyrrole ($1.5 \cdot 10^{-1}$ mol), thus in 50% excess 50 ml of treated and distilled THF.

The chlorinated bielectrophile (11.55 g, $0.5 \cdot 10^{-1}$ mol) in solution in 40 ml of THF is added dropwise under argon. The mixture is left stirring at ordinary temperature for 20 hours. The THF is then evaporated, the residue is taken up in ether, washing is carried out with water, separation is carried out by settling, drying is carried out and evaporation is carried out. 16 g of oily liquid are then vacuum distilled, making it possible to obtain 11 g of monomer (III) (Yield: 75% with respect to the dichlorinated derivative).

Figure 1B:
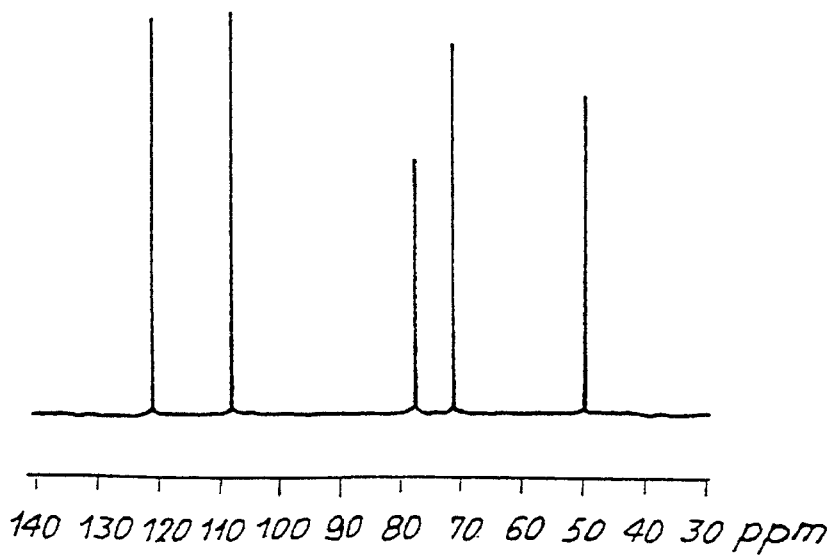

NMR spectra of the product obtained are shown in FIG. 1.

B) Conditions Suitable for the Electrochemical Polymerization of the Monomers (III)

Two methods of polymerization are described below:

1. Constant-potential electrolysis on a platinum sheet 1.2 g of monomer (III) (m=3) is dissolved in 25 ml of methylene chloride containing 0.1M $Bu_4NBF_4$. This solution constitutes the anolyte arranged in a compartment of a U-cell containing a second compartment (volume 20 ml). The two compartments are separated by a sintered component with a porosity of 3. The anode consists of a platinum sheet with a total surface area of 20 cm². The cathode is made of graphite (immersed surface area 15 cm²). A controlled potential of +1.0 V is applied to the anode. A current of 150 mA passes for 3 h 30 and 180 mg of a shiny black conductive deposit are obtained.

Figure 3:
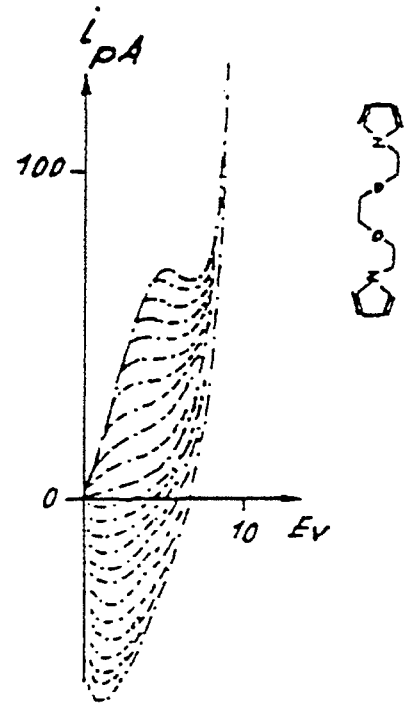
FIG. 3 is a diagram illustrating the monitoring of the formation of the polymer layer in the electrolysis cell in the course of operation.

The formation of a conductive polymer from III (m=2) can be demonstrated by cyclic voltametry (FIG. 3) under the following conditions: concentration $5 \cdot 10^{-3}$ mol·$l^{-1}$. Electrolyte: acetonitrile containing 0.1 mol·$l^{-1}$ $Bu_4NBF_4$. Polished platinum microanode (surface area: 0.87 mm²). Sweep rate: 0.5 V·$s^{-1}$. Potentials shown with reference to the 0.1M Ag/AgNO₃ systems. Development of the deposit during the first 27 sweeps (the steady progression of the film, whose redox response is at +0.5 V, will be noted).

2. Constant-current electrolysis on graphite beads or grains

A solution of $1.7 \cdot 10^{-2}$ mol/l of (III) (m=3) in acetonitrile containing 0.1M Bu₄NBF₄ is placed in an electrolysis cell of Priam type 1. Circulation of the electrolyte is kept constant during the polymerization operation at a flow rate of 2 l/min.

Figure 2:
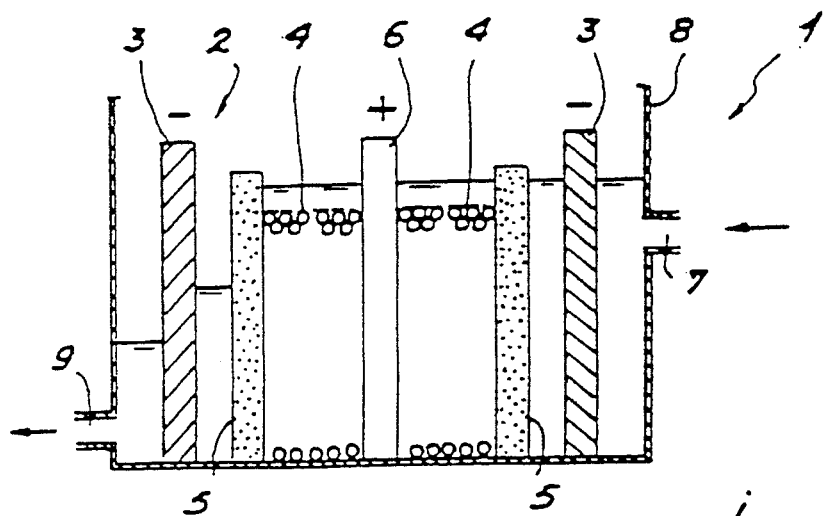
FIG. 2 is a diagram of an electrolytic cell capable of being used for the production of a polymer in accordance with the invention, particularly in the supported state on a conductive support.

An electrolysis cell 1 of this type has been shown schematically in FIG. 2.

A cathode 2 is composed either of one or a number of stainless steel grid(s) 3 (apparent surface area: 1 dm²) or alternatively of a carbon paper (for example the paper product from Carbon Lorraine). The oil coke 4 (total mass: 50 g) is arranged at the centre of the case to form a voluminous anode between two porous walls 5 acting as spacer. The anodic current supply is a titanium grid 6 covered with irridium oxide.

The electrolyte 7 enters at the upper part of the retaining vessel 8 and departs at the lower part 9 of the other side.

Figure 4:
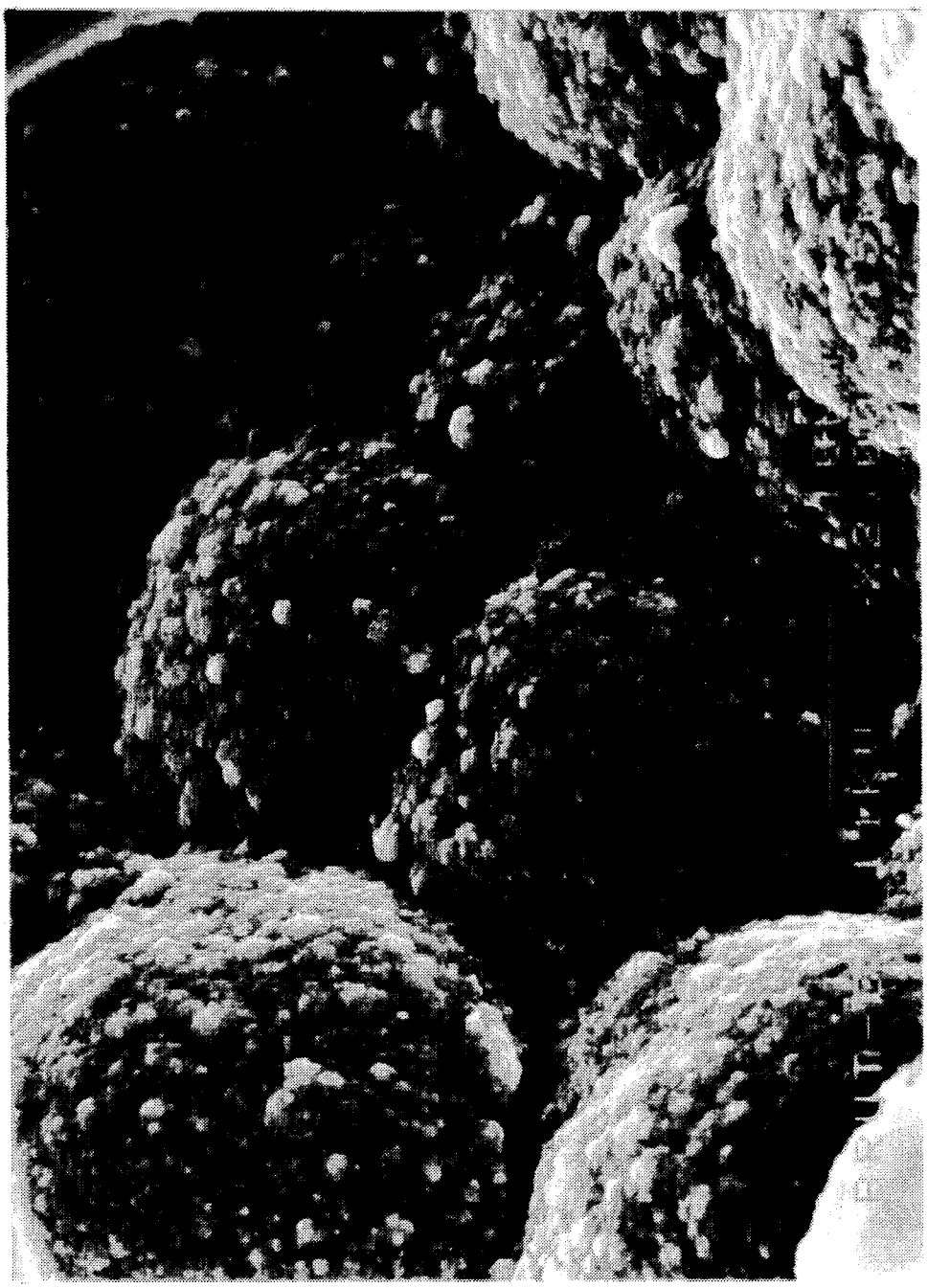
FIGS. 4 and 5 are reproductions of photographs showing the morphology of polymer deposits obtained on graphite grains under the conditions described in the example, after dedoping with $Bu_3N$ contained in $CH_3CN$, at different magnifications, respectively 18,700 and 16,000 times. The samples were gilded with fine gold.
Figure 5:
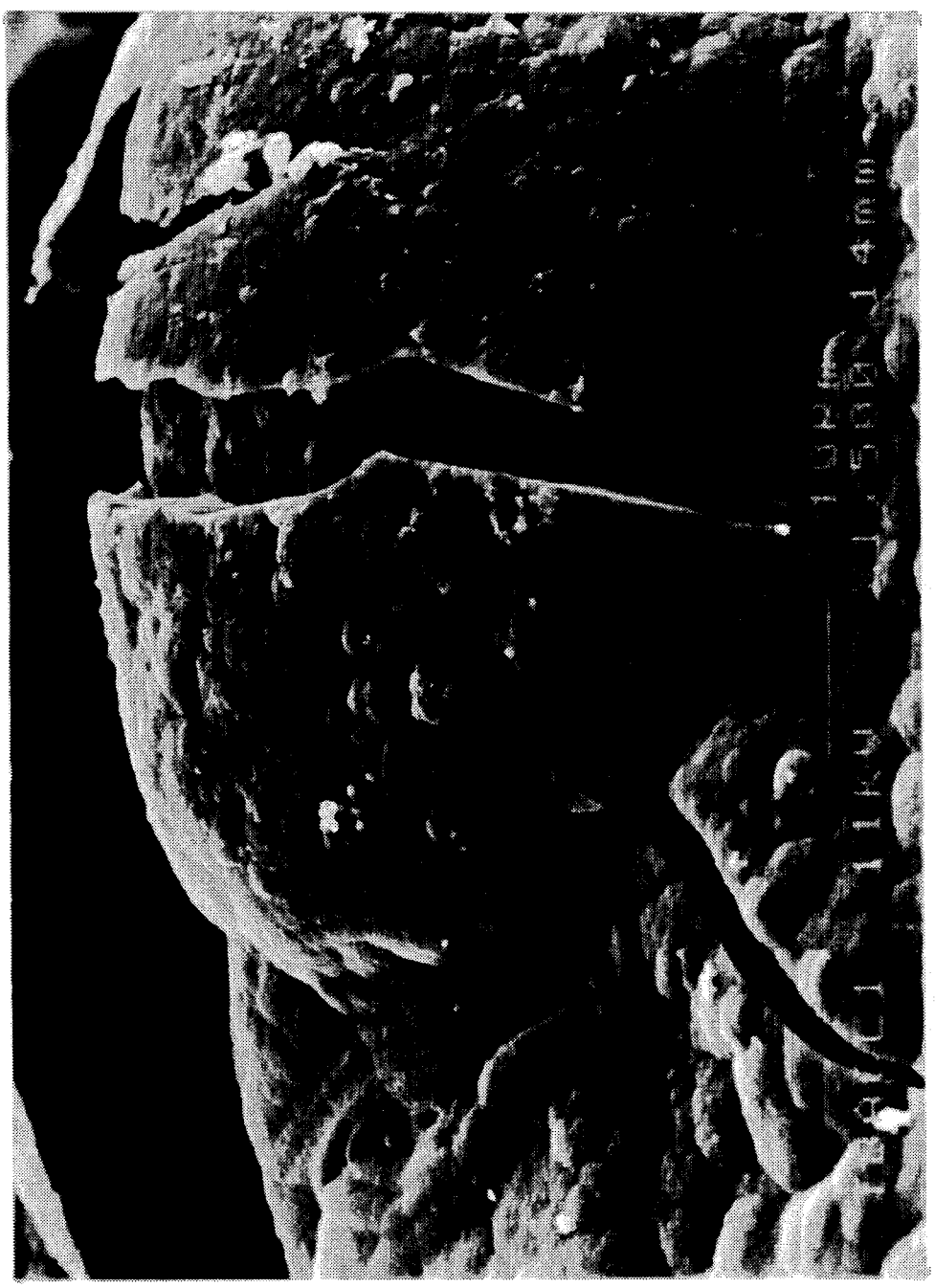

The current imposed is 0.6 A for 6 hours. In this case, the polymer deposit obtained is 3.5 g. It is characterized by PER, IR and SEM (FIGS. 4 and 5).

The values given above are given by way of example and are in no way limiting.

With respect to a polymerization by constant-potentional electrolysis, a polymerization by constant-current electrolysis is representative of a preparation in an industrial environment. Moreover, as will be seen subsequently, the electrolysis technique used makes it possible to prepare directly elements which will then be assembled in order to form units for the recovery of metal cations by encapsulation with polymer resins.

3. Reduction and dedoping of the conductive deposits

As was explained in prior documents (3,4), it is necessary to reduce the polymer in order to remove part of the anions arising from the electrolyte. This reduction can be carried out chemically or electrochemically. It has been shown that the dedoping of the polymer was more complete and simpler by the chemical route than by the electrochemical route. Moreover, this technique can be applied to all the polymers synthesized.

Dedoping of the deposits on a metal plate or on carbon can be easily obtained [lacuna] treatment after the end of the electrolysis. Washing with acetonitrile and drying in a vacuum oven at a temperature <100° C. The treatment can be carried out with commercial tetrabutyl- or tetraethyl ammonium hydroxides (source Fluka or Aldrich) at a concentration of $10^{-1}$ or $10^{-2}$M in acetonitrile. The reduction can also be carried out with tertiary amines, ammonium superoxides (prepared in situ by electrolysis of oxygen) or alkali metal superoxides (potassium superoxide).

Neveretheless, it seems necessary for any application relating to an extraction of metal cations to subject to a treatment with tetraalkylammoninm hydroxide, which makes the exchange between ammonium ions and metal ions easier.

The polymers formed from pyrrole ethers of type III (using the ability of pyrrole to polymerize at the 2,2'-positions) have mesh structures possessing a (probably large) number of polyether sites.

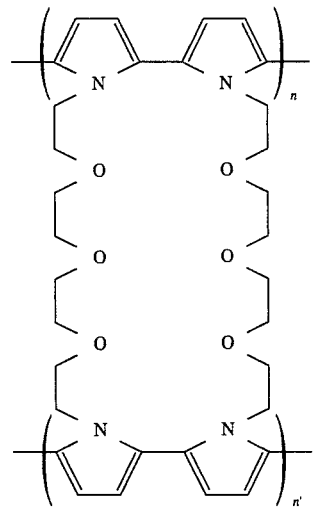

The anodic method thus makes it possible easily to form sites containing 2, 4, 6, 8 or 10 oxygen atoms. Moreover, mixed electrolyses of two monomers can easily modulate the size of the sites.

Example:

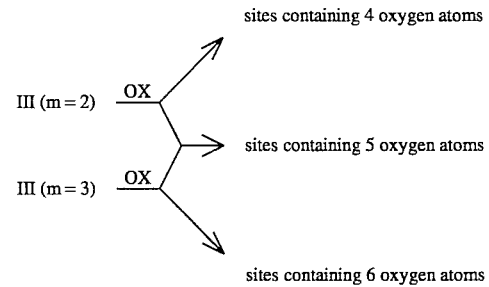

Moreover, the formation of macrosites from no longer 2 but 3, indeed 4, monomers is not ruled out and can contribute to applications in the extraction of complex cations. Example for (III), m=2:

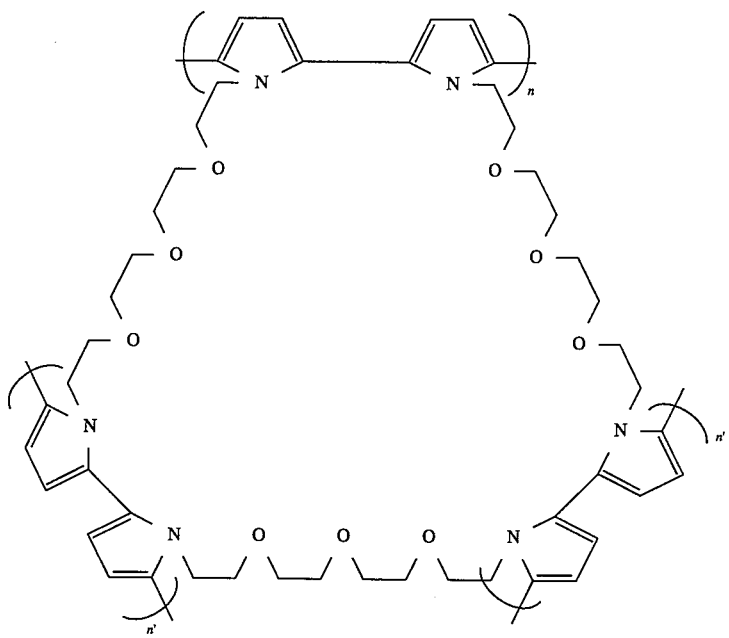

The possibility of obtaining not only these resins in the doped form but in the neutral form is also claimed.

These reduced polymers in the neutral form can behave as ion-exchange resins and particularly have the property of extracting metal ions present in aqueous or organic solutions, provided that the resins are treated beforehand with ammonium salts (operation as ion-exchange resin). The affinity of the resins for alkali metal ions, alkaline-earth metal ions, the silver ion and precious metal ions is claimed.

C) Industrial Production and Use of the Polymeric Resins Synthesized

The method of industrial synthesis used may be that described in paragraph 2, i.e. a constant-current electrolysis on graphite beads. In fact, the use of voluminous anodes within which circulates the electrolyte charged with monomer units will make it possible, during the electrolysis, to obtain porous elements highly charged in "encapsulating" polymeric resins. At the end of electrolysis, dedoping of the polymer units is carried out in the same reaction loop.

If the electrolysis reactor used is a reactor containing voluminous electrodes, it is sufficient, after dedoping the polymer, to remove the voluminous anodes from the electrolysis vessel, to remove the current supply and then to enclose the top of the assembly in polypropylene which contains carbon granules coated with polymer resin. It then suffices to combine a number of voluminous anodes in an appropriate receptacle in order to form a porous stack capable of encapsulating metal cations present in low concentrations in industrial effluents.

The depletion in metal ions will be carried out by a simple percolation in this stack.

The present invention also relates to a process for the manufacture of a filter cartridge for the purification and/or recovery of metal ions contained in a solution, characterized in that polymer units are produced, by constant-current electrolysis, from an electrolyte charged with monomer units of the type described above and particularly consisting of a polyether carrying pyrrole or thiophene units bonded to the ends of the chains of this polyether via, for each of these heterocyclic compounds, either their carbon atoms in the 3,3'-positions of their heterocycles or, as regards more particularly the pyrrole groups, their respective nitrogen atoms, the 2- and 2'-positions of these heterocycles being, however, free of all substitutions or, at the very most, substituted by easily removable groups, on a carbon-based conductive support material contained in a reservoir possessing porous walls belonging to a voluminous anode, at the end of electrolysis, the polymer units thus obtained are dedoped in the same reaction loop, after dedoping the polymer units, the means for supplying the current of the reservoir are removed, and then the said reservoir, which contains the support material coated with polymer units, is sealed off in order to thus obtain the said filter cartridge.

Finally, the present invention relates to a filter for the purification and/or recovery of metal ions, more particularly of heavy metals such as silver, contained in solutions brought into contact with it, characterized in that it comprises at least one filter cartridge comprising a reservoir possessing porous walls containing a conductive material, particularly carbon-based, coated with polymer resin of the type described above and especially with polymer resin characterized by polymeric chains containing a plurality of pyrrole or thiophene rings, if appropriate both at the same time, and interconnected to each other via 2,2'- bonds, on the one hand, and polyether chains corresponding in particular to the formulae —CH$_2$—(—CH$_2$—O—CH$_2$—)$_m$—CH$_2$— with m equal to 3, 4 or 5, these chains being themselves bonded, via their own ends, either to the carbon atoms in the 3,3'- positions respectively of these pyrrole or thiophene rings or, in the case of the pyrrole rings, to their nitrogen atoms.

Figure 6:
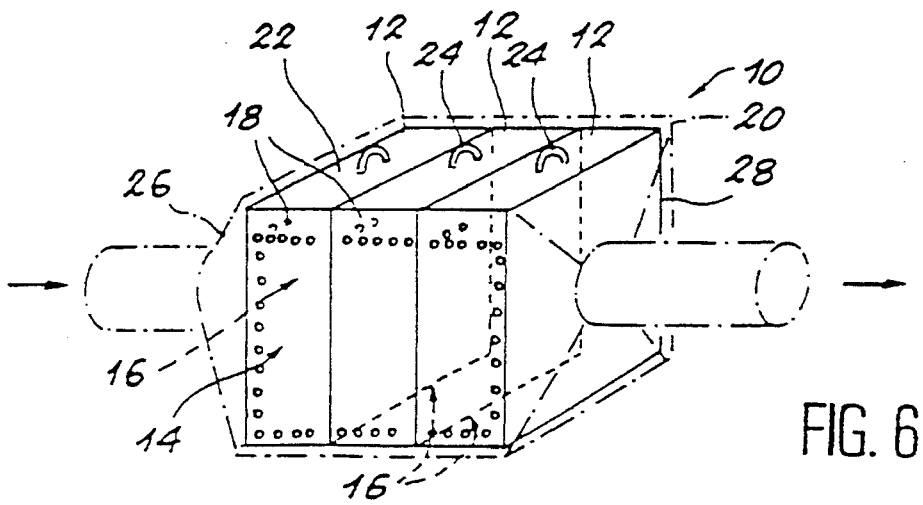
FIG. 6 shows a diagram of an embodiment of a filter constituted by implementing the process for the production of a polymer according to the invention.

FIG. 6 schematically shows an embodiment of such a filter 10 according to the invention comprising three identical filter cartridges 12, for example of parallelepiped shape.

Each cartridge comprises a side bracing 14 made of rigid material for structural maintenance of the cartridge and two rectangular walls 16 made of porous material, for example of polypropylene, and the cartridges contain a carbon-based conductive material 18 coated with polymer resin of the type according to the invention.

The filter comprises a parallelepiped casing 20 (chain-dotted line in the figure), for example made of stainless steel, containing the three cartridges.

It is equipped with a removable upper plate 22, which makes it possible to remove and replace the filter cartridges, equipped, in the upper part, with a grasping handle 24.

Moreover, the filter comprises a section, for example tronconic 26, for entry of the liquid to be decontaminated and an identical section 28 for departure of the liquid after decontamination.

Such a filter makes it possible, for example, to obtain continuous decontamination of effluent charged with radioactive Ag110 with a flow rate of the order of m³/h.

REFERENCES (1) J. Simonet and J. Rault-Berthelot, Prog. Solid St. Chem., (1991), 21, 1–48 (and references cited).

(2) V. Le Berre, L. Angely, N. Simonet-Gueguen and J. Simonet, J. Electroanal. Chem., (1986), 206, 115.

(3) J. Simonet and C. Saboureau, French Patent Application (1990).

(4) Y. Gache and J. Simonet, J. Chim. Phys., (1992), 89, 1027.

I claim:

1. A process for the manufacture of a filter cartridge for the purification and/or recovery of metal ions contained in a solution, wherein polymer units are produced, by constant-current electrolysis, from an electrolyte charge with monomer units comprising an aliphatic polyether chain containing at least three ether units and pyrrole or thiophene heterocyclic units bonded to ends of the chain via, for each of said heterocyclic units either carbon atoms in the 3,3'-positions of the heterocyclic units or, with respect to the pyrrole heterocyclic units, via the respective nitrogen atoms, the 2- and 2'-positions of said heterocyclic units being free of all substituents or substituted by easily removable protective groups, on a carbon-based conductive support material contained in a reservoir possessing porous walls belonging to a voluminous anode; at the end of electrolysis, the polymer units thus obtained are dedoped to remove anions arising from the electrolyte; after dedoping the polymers units, means for supplying the current of the reservoir are removed; and then the reservoir, which contains the support material coated with polymer units, is sealed off in order to obtain the filter cartridge.

2. A filter for the purification and/or recovery of metal ions including silver ions, contained in solutions brought into contact with the filter, said filter comprising a cartridge including a reservoir possessing porous walls, said reservoir containing carbon-based material coated with a polymer resin comprising a polymer having repeating units containing a plurality of aliphatic polyether chains, each chain bonded at its ends with a heterocyclic unit consisting of at least one member selected from the group consisting of pyrrole and thiophene rings, the heterocyclic units at each of different polyether chains being interconnected to each other via the 2,2'-positions of the heterocyclic rings and said aliphatic polyether chains having the formula:

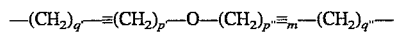

with q' and q" being, independently of one another, equal to 1 or 2, p and p" being, independently of one another, equal to 1 or 2; and m being equal to 3, 4 or 5;

said chains being bonded either to carbons at the 3,3'-positions respectively of the pyrrole or thiophene units or with regard to the pyrrole units to nitrogen atoms.

3. A filter according to claim 1, wherein said filter further comprises a casing containing said cartridge.

4. A filter according to claim 2, wherein said filter comprises a plurality of cartridges which can be removed from said casing for replacement.

* * * * *